(12) United States Patent
Williams (10) Patent No.: US 11,299,190 B2
(45) Date of Patent: Apr. 12, 2022

(54) INFANT CAR SEAT CHALLENGE TESTING STATION

(71) Applicant: ARTi, Inc., Hampton, VA (US)

(72) Inventor: Rosemary Evans Williams, Williamsburg, VA (US)

(73) Assignee: ARTI, INC., Hampton, VA (US)

( * ) Notice: Subject to any disclaimer, the term of this patent is extended or adjusted under 35 U.S.C. 154(b) by 36 days.

(21) Appl. No.: 16/951,427

(22) Filed: Nov. 18, 2020

(65) Prior Publication Data

US 2021/0070342 A1 Mar. 11, 2021

Related U.S. Application Data

(63) Continuation-in-part of application No. 16/449,656, filed on Jun. 24, 2019, now abandoned.

(51) Int. Cl.
| | |
|---|---|
| *B62B 5/08* | (2006.01) |
| *B60N 2/28* | (2006.01) |
| *B62B 3/04* | (2006.01) |
| *A61B 5/08* | (2006.01) |

(52) U.S. Cl.
CPC ............ *B62B 5/082* (2013.01); *B60N 2/2806* (2013.01); *B60N 2/2842* (2013.01); *B62B 3/04* (2013.01); *A61B 5/0826* (2013.01); *A61B 2503/04* (2013.01)

(58) Field of Classification Search
CPC ......... B62B 5/082; B62B 3/04; B60N 2/2806; A61B 5/0826; A61B 2503/04
See application file for complete search history.

(56) References Cited

U.S. PATENT DOCUMENTS

| | | | | |
|---|---|---|---|---|
| 3,016,275 | A * | 1/1962 | Grant ................. | A61G 13/0018 108/93 |
| 5,509,810 | A * | 4/1996 | Schertz .................. | G09B 23/28 600/587 |
| 2010/0122414 | A1* | 5/2010 | Shah ..................... | A61G 13/122 5/637 |
| 2011/0113555 | A1* | 5/2011 | Smith .................... | A61G 11/00 5/601 |
| 2013/0158339 | A1* | 6/2013 | Cipriano ................ | G16H 40/63 600/22 |
| 2017/0166228 | A1* | 6/2017 | Newton .................... | B62B 1/12 |
| 2017/0258244 | A1* | 9/2017 | Waldman ............... | A47D 1/023 |

* cited by examiner

*Primary Examiner* — Brian L Swenson
(74) *Attorney, Agent, or Firm* — Peter J. Van Bergen (57) ABSTRACT

A station for conducting an infant car seat challenge test includes a first portion, a second portion, and a resilient cushion. The first portion has a top configured as an open-top receptacle. The resilient cushion is disposed in and is coupled to the open-top receptacle. The resilient cushion has a sloped top surface where the sloped top surface is sloped towards a first side of the open-top receptacle. The resilient cushion is adapted to support an infant car seat thereon. The second portion is coupled to the first portion at a second side of the open-top receptacle. The second portion includes a platform positioned above the open-top receptacle wherein the platform is adapted to support an electronic display thereon.

20 Claims, 8 Drawing Sheets

INFANT CAR SEAT CHALLENGE TESTING STATION

This is a continuation-in-part application of co-pending application Ser. No. 16/449,656, "INFANT CAR SEAT CHALLENGE TESTING STATION", filed on Jun. 24, 2019.

FIELD OF THE INVENTION

The present technology is related to car seat testing for infants prior to discharge from a hospital or other medical facility. More particularly, the present invention relates to a station for conducting an infant car seat challenge test.

BACKGROUND OF THE INVENTION

Car seats reduce mortality and morbidity associated with automobile accidents in infants and children, and are required throughout the United States and in other countries. Car seats should always be used, including the initial automobile ride. Commercially available infant seats offer the optimum protection for healthy babies born at term. There are some children who many need special care beds, however, which provide protection for special needs infants. Hypoxemia related to positioning and apneic episodes are common in infants born before term in whom apnea may persist up to and beyond term gestation. Pre-discharge respiratory recordings in very low birth weight infants may reveal significant apnea in many babies otherwise ready for discharge. The use of car seats is recommended for all babies during automobile travel, but this may expose preterm infants to other potential risks.

The American Academy of Pediatrics (AAP) recommends that all preterm neonates undergo a period of observation in a car safety seat before discharge, known as the Infant Car Seat Challenge (ICSC), to monitor for respiratory immaturity and the risk of adverse cardiopulmonary events in the upright position. This observation in a car seat before discharge is designed to monitor for possible apnea, bradycardia or oxygen desaturation.

Car seat testing is usually done in the hospital within one week before your baby is ready to go home. The infant will be placed in a car seat (preferably the car seat brought in by the parents that will actually be used to transport the infant). The infant will remain seated in the car seat for 90 to 120 minutes or the length of the car ride home, whichever is longer. During the test, the infant's heart rate, breathing and oxygen level are monitored in accordance with the guidelines of the ICSC. There is currently no device configured specifically to meet the needs of care givers testing a child during the ICSC.

In the medical community, carts are configured to store, carry, and transport medical supplies, equipment, materials, and other items in a variety of different patient settings (e.g., doctor's office, hospital, etc.). And while there are protocols and procedures in place to test children and especially small infants, there are obstacles to providing testing that accommodates both the medical needs of the children and the need to provide adequate and comprehensive ICSC testing. There is a need, therefore, to provide a means to assess children and infants restricted to child car seats in order to adequately assess the ability of children with special or defined needs to the rigors of transport through various means; primarily in cars and other personal vehicles, but other means of transport are directly impacted by the need to safely and securely transport children and infants.

SUMMARY OF THE INVENTION

In accordance with the present invention, a station for conducting an infant car seat challenge test includes a first portion adapted to be positioned on a horizontal surface. The first portion has a top configured as an open-top receptacle. A resilient cushion is disposed in and is coupled to the open-top receptacle. The resilient cushion has a sloped top surface where the sloped top surface is sloped towards a first side of the open-top receptacle. The resilient cushion is adapted to support an infant car seat thereon wherein the infant car seat is positioned such that an infant seated in the infant car seat faces the first side of the open-top receptacle. A second portion of the station is coupled to the first portion thereof at a second side of the open-top receptacle. The second portion includes a platform positioned above the open-top receptacle wherein the platform is adapted to support an electronic display thereon.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

The following disclosure describes various types of medical carts and associated apparatuses and methods. Certain details are set forth in the following description where FIGS. 1-5 illustrate an embodiment of the present invention. Other details describing well-known structures and systems often associated with medical carts, however, are not set forth below to avoid unnecessarily obscuring the description of the various embodiments of the disclosure.

Many of the details and features shown in the Figures are merely illustrative of particular embodiments of the disclosure. Accordingly, other embodiments can have other details and features without departing from the spirit and scope of the present disclosure. In addition, those of ordinary skill in the art will understand that further embodiments can be practiced without several of the details described below. Furthermore, various embodiments of the disclosure can include structures other than those illustrated in the Figures and are expressly not limited to the structures shown in the Figures. Moreover, the various elements and features illustrated in the Figures may not be drawn to scale.

In the Figures, identical reference numbers identify identical or at least generally similar elements. To facilitate the discussion of any particular element, the most significant digit or digits of any reference number refer to the Figure in which that element is first introduced. For example, element 50 is first introduced and discussed with reference to FIG. 1.

Figures 1, 2:
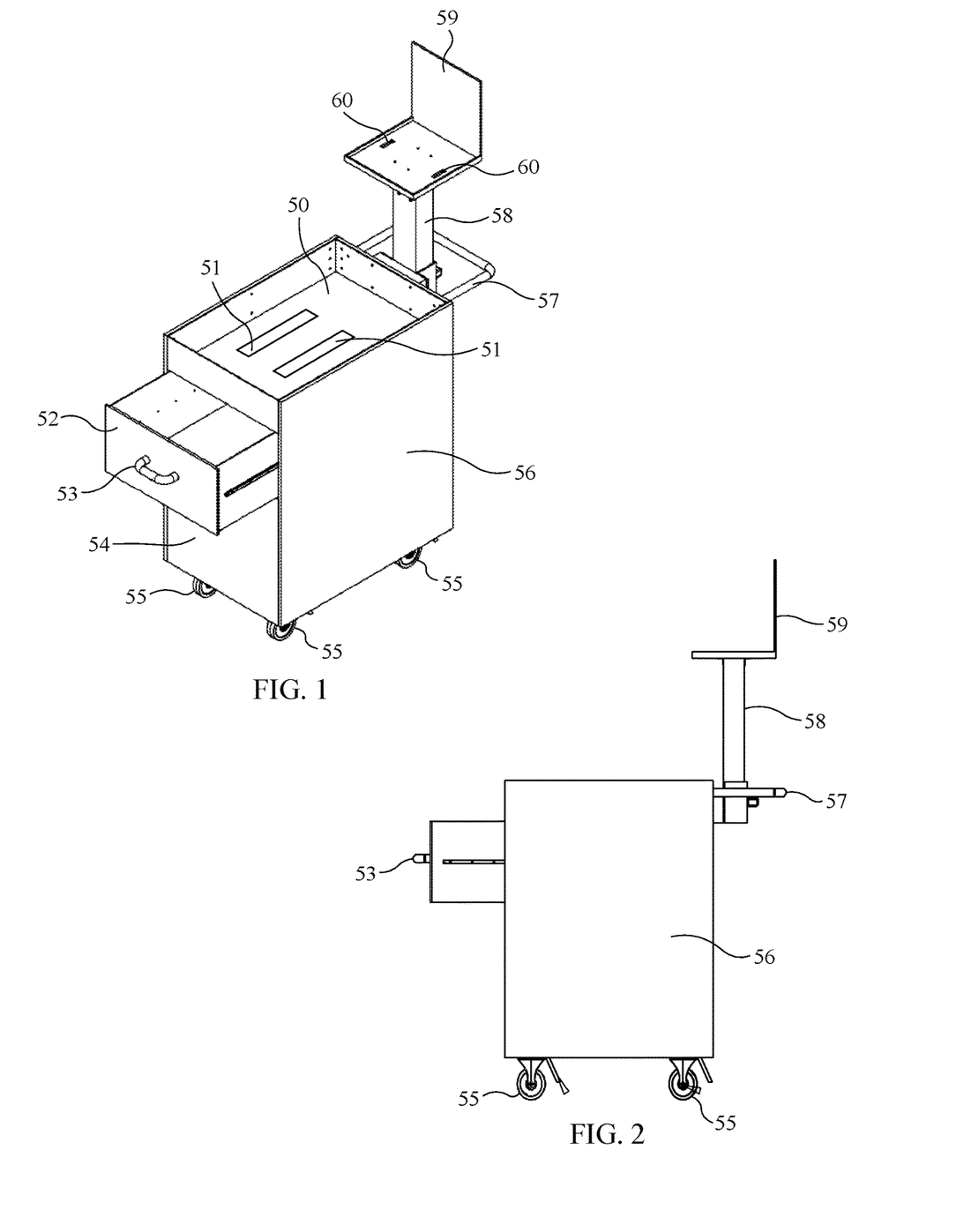
FIG. 1 is an oblique view of a medical cart configured in accordance with an embodiment of the present invention.
FIG. 2 is a side view of the medical cart configured in accordance with an embodiment of the present invention.
Figure 4:
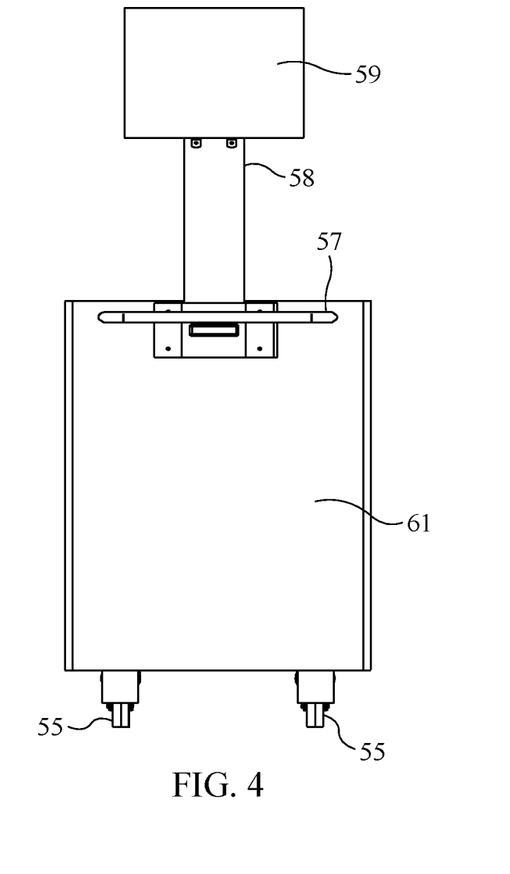
FIG. 4 is a rear view of the medical cart configured in accordance with an embodiment of the present invention.

FIG. 1 shows an embodiment of an infant car seat challenge testing station (the "station") having a car seat holding area 50, the car seat holding area 50 further comprising one or more holes 51, the one or more holes 51 being configured to allow adhesive straps such as Velcro (not shown) to be passed through the one or more holes 51. The station has a front panel 54, side panels 56, and a back panel (FIG. 4, 61). The station as shown further comprises one or more storage compartments 52 disposed within the front panel 54, as shown comprising a drawer with a handle 53. It will be understood, however, that the one or more storage compartments, while shown with a drawer, may be open storage recesses, open storage recesses with doors or other covering means, or other configurations that are well known in the art. The station further comprises wheels 55. In a preferred embodiment, the wheels 55 will be chosen from the group of wheels that include locking mechanisms so that the station can be locked in place while in use. The station as shown also comprises a handle 57 to be used to maneuver the station. A bracket 59 is also provided to hold monitoring equipment (not shown), which further includes one or more holes 60 to receive one or more straps (not shown) to secure monitoring equipment when in use. It will be understood that the use of the one or more holes 51 in the car seat holding area 50 in conjunction with straps allows the station to be used with various designs of infant car seats. It will also be understood that the use of the one or more holes 60 in the bracket 59 allows the station to be used with various types of monitoring equipment.

The bracket 59 is moveably attached to the station with a telescoping arm 58. Telescoping arms are well known in the art, and it will be understood that various types and designs of telescoping arms may be utilized to attach the bracket 59 to the station without deviating from the scope and intent of the invention as described herein. For example, a telescoping arm may be chosen that moves vertically (as shown) in relation to the station, an articulated arm that provides ranges of motion for the bracket 59 in relation to the station, or other well known means.

FIG. 2 shows a side view of an embodiment of the present invention, detailing the configuration of the telescoping arm 58 affixed to the station and the bracket 59. As shown the telescoping arm 58 is fully extended up. The drawer 52 is also shown partially disposed within the station.

Figure 3:
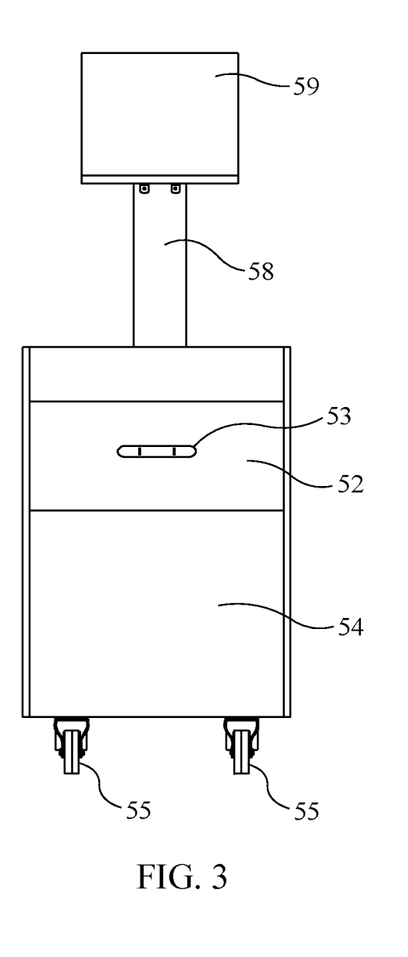
FIG. 3 is a front view of the medical cart configured in accordance with an embodiment of the present invention.

FIG. 3 shows a front view of an embodiment of the present invention, and FIG. 4 shows of view of an embodiment of the present invention as seen from the back.

Figure 5:
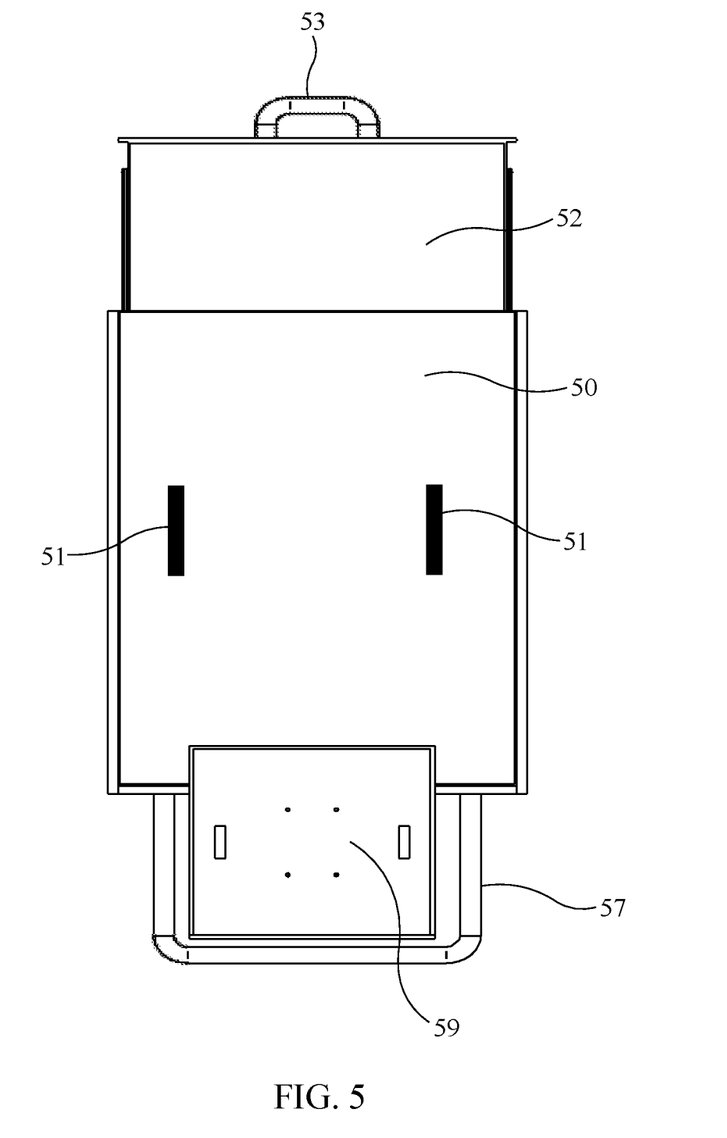
FIG. 5 is a top view of the medical cart configured in accordance with an embodiment of the present invention.

FIG. 5 shows a top-down view of an embodiment of the present invention. As shown, the car seat holding area 50 has two holes 51 through which straps or other restraining means (not shown) may be disposed to facilitate restraining of an infant car seat during testing. The bracket 59 is also shown, as is the drawer 52 partially disposed within the station.

Figure 6:
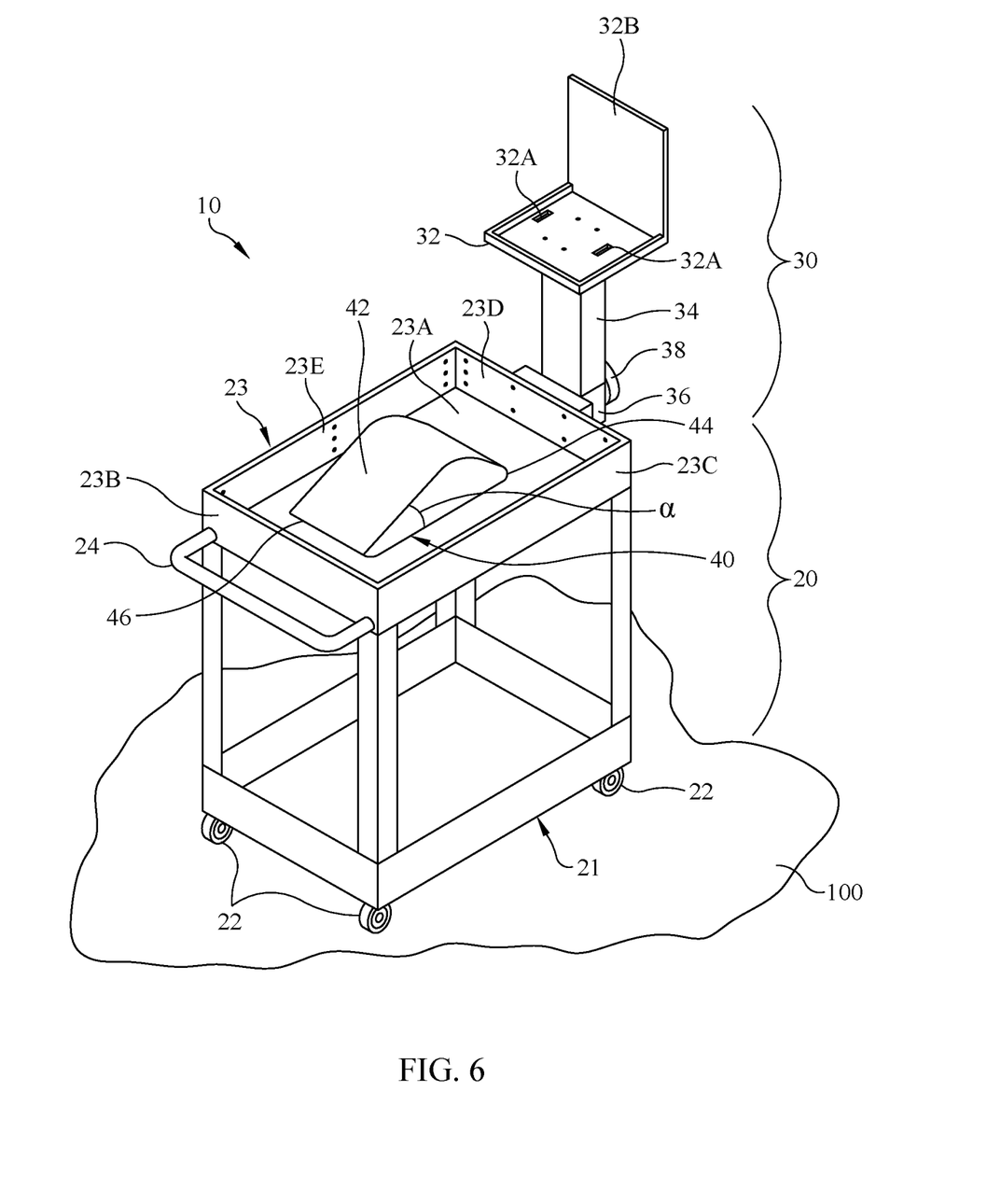
FIG. 6 is a perspective view of an infant car seat challenge testing station in accordance with another embodiment of the present invention.
Figure 7:
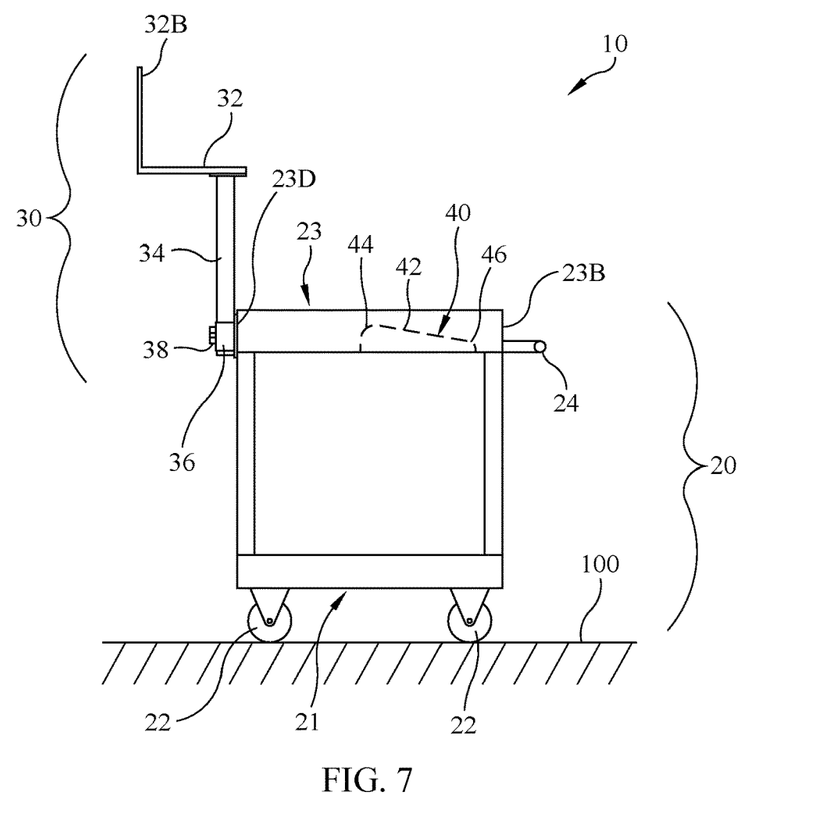
FIG. 7 is a side view of the testing station illustrated in FIG. 6.

Another embodiment of the present invention will now be described with simultaneous reference to FIGS. 6-7 where an infant car seat challenge testing station is referenced generally by numeral 10. Station 10 includes a lower portion or base 20, an upper portion 30 coupled to base 20, and a resilient cushion 40 coupled to base 20. Base 20 can be positioned and movable on a horizontal surface 100 such as a floor in a medical facility. In the illustrated embodiment, base 20 is an open-frame cart generally made from material(s) acceptable for use in a medical facility. Base 20 has a bottom deck or tray 21 supported by wheels 22 (e.g., lockable wheels) on surface 100. At the top of base 20 is an open-top receptacle 23 having a floor 23A and side walls 23B-23E coupled to and extending up from the periphery of floor 23A. Base 20 is configured such that floor 23A is parallel to surface 100. Floor 23A can be rectangular as shown such that side walls 23B and 23D directly oppose one another at opposing ends of floor 23A. To facilitate movement of base 20 on surface 100, a handle 24 can be coupled to a portion of base 20 at the side thereof shared by side wall 23B.

Coupled to base 20 is upper portion 30 that includes a platform 32 similar to the above-described bracket 59. Platform 32 can include mounting features such as holes 32A and a back stop 32B for the secure positioning and mounting of a display/monitor, laptop computer, etc. (not shown) on platform 32. Platform 32 is generally positioned above open-top receptacle 23 using a support pole 34. In the illustrated example, support pole 34 is adjustable in height relative to open-top receptacle 23. Such height adjustment is facilitated and set at a bracket 36 coupled to side wall 23D. Bracket 36 includes a set screw/knob 38 that can be loosened/tightened to adjust/set the height of platform 32 as would be understood in the art. Support pole 34 can be rectangular as shown, but could also be cylindrical to facilitate the pivoting of platform 32 during mounting and/or viewing of a display mounted on platform 32.

Resilient cushion 40 is disposed within open-top receptacle 23 and is coupled to floor 23A thereof. Cushion 40 presents a firm but resilient structure similar to that of a car's back seat on which an infant car seat (not shown) would be placed by a parent or care giver. In addition to its resilient structure, cushion 40 defines a sloped surface 42 that mimics the slope angle of a car's back seat on which an infant car seat will be placed. To achieve sloped surface 42, one end 44 of cushion 40 is thicker than its opposing end 46. Cushion 40 is positioned on floor 23A such that sloped surface 42 slopes towards side wall 23B, i.e., thicker end 44 opposes and is spaced apart from side wall 23D while thinner end 46 opposes and is spaced apart from side wall 23B. Thicknesses of ends 44 and 46 are selected such that the slope angle α that sloped surface 42 makes with floor 23A is in the range of approximately 6° to 17°. That is, end 44 simulates a relative height of a car back seat's edge while end 46 simulates the relative height of a car back seat where the seat meets a back seat's backrest.

In operation, a display or laptop (not shown) is mounted on platform 32 such that it is readily viewable by a challenge test operator (not shown) who is generally positioned adjacent to the side of station 10 that includes side wall 23B of open-top receptacle 23. An infant car seat (not shown) is placed on cushion 40 such that the infant car seat's seating area opens/faces towards side wall 23B, i.e., side wall 23B represents the rear end of a car since infant car seats must face the rear of a car when used. Accordingly, an infant placed in a car seat so-positioned on station 10 will face towards side wall 23B. Station 10 with its cushion 40 positions an infant in their infant car seat at an angle they would experience just as if they would in the back seat of a car. This simulated positioning is critical for the performance of an effective challenge test since an infant's head position is very easily affected by the angular orientation of its body. Given that an infant's head position can greatly impact a variety of critical body functions, station 10 provides a critical realistic body-positioning environment for an effective challenge test.

Figure 8:
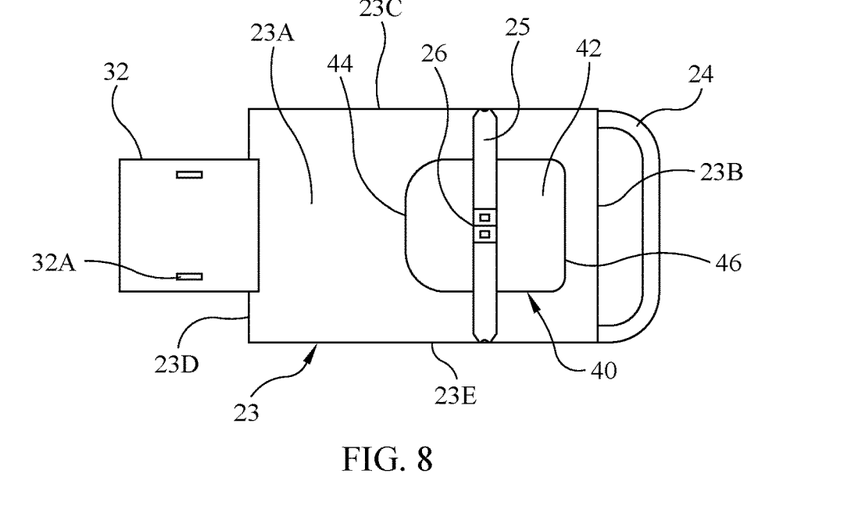
FIG. 8 is a top view of an infant car seat challenge testing station in accordance with another embodiment of the present invention.

Another embodiment of the present invention is shown in FIG. 8 where a top view of the above-described station 10 further illustrates a strap 25 that can be coupled to open-top receptacle 23 at floor 23A and/or opposing side walls 23C and 23E. Strap 25 can include a buckle 26 similar to a car's seat belt. Strap 25 can be used to secure an infant car seat in position on cushion 40.

Figure 9:
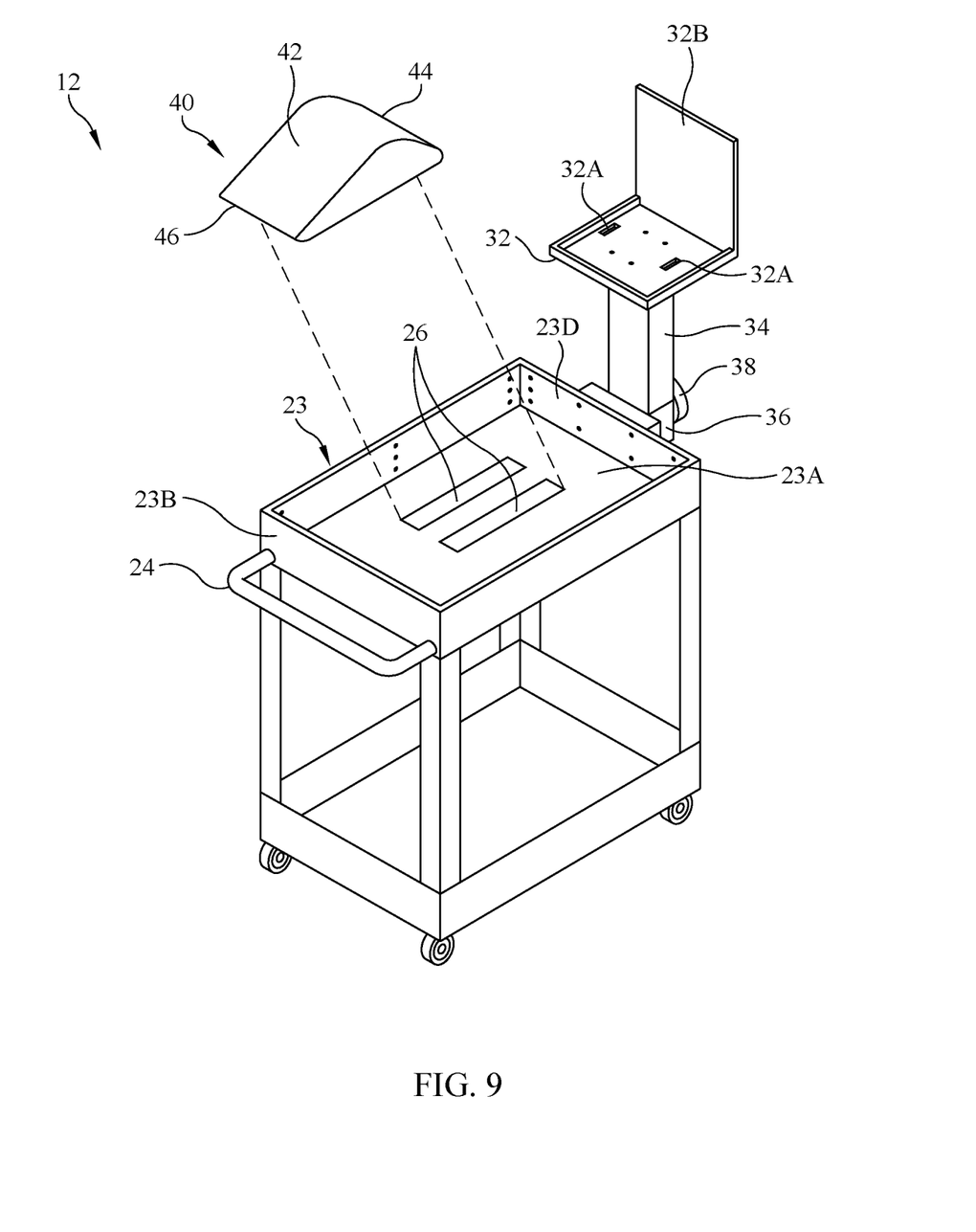
FIG. 9 is a perspective view of an infant car seat challenge testing station having a removable resilient cushion in accordance with another embodiment of the present invention.

FIG. 9 illustrates another infant car seat challenge station 12 that supports resilient cushion 40 in a way that allows it to be readily coupled to floor 23A and removed therefrom. For example, in the illustrated embodiment, one or more pieces of hook-and-loop fastener material 26 can be coupled to floor 23A such that cushion 40 can be attached to and removed from material 26 via cooperative hook-and-loop fastener material (not shown) mounted on the underside of cushion 40. Such hook-and-loop fastening systems are well-known in the art. Making cushion 40 readily attachable/removable facilitates cleaning of station 12, positioning of cushion 40 to accommodate a variety of infant car seat designs, and/or replacement of cushion 40.

Figure 10:
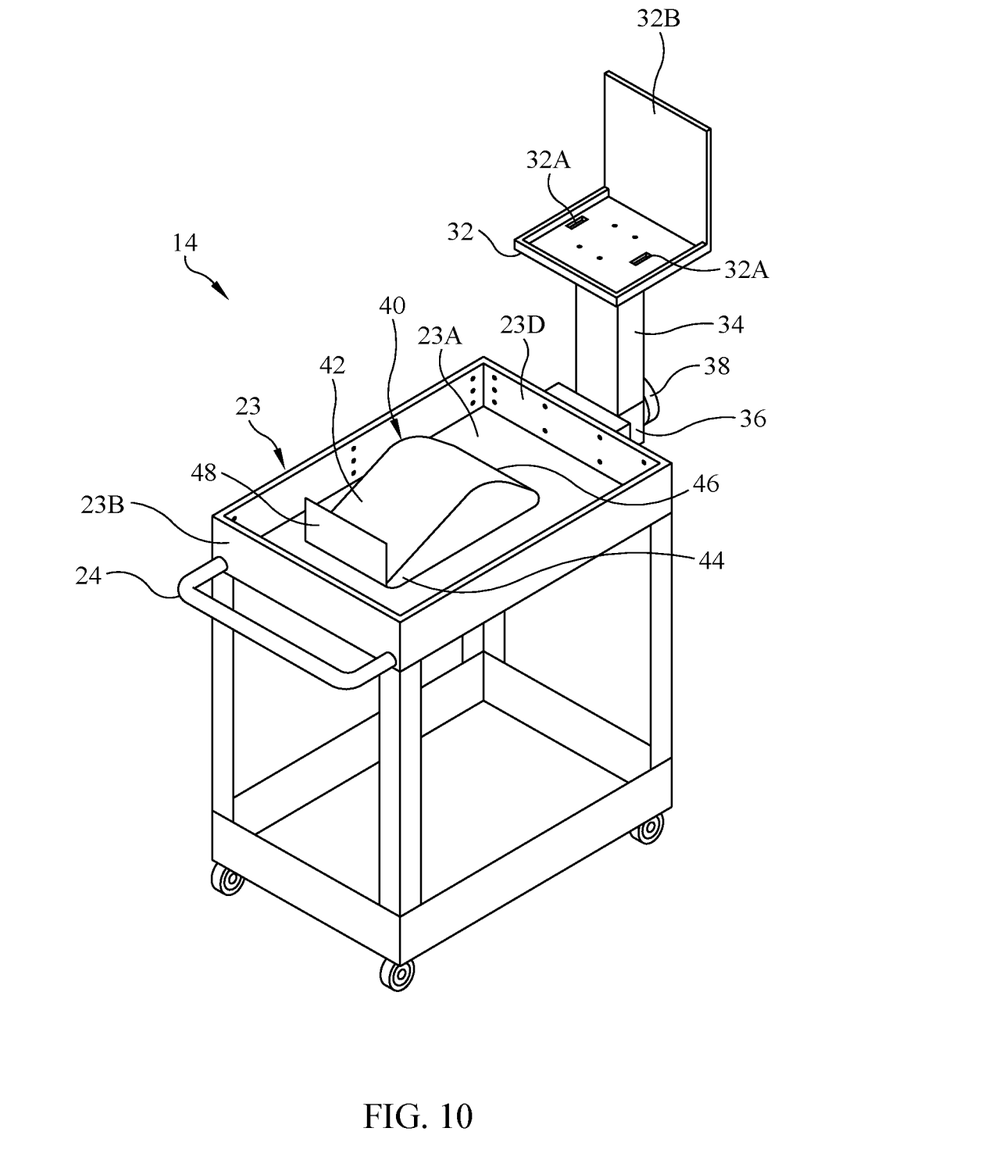
FIG. 10 is a perspective view of an infant car seat challenge testing station having a seat-back simulating stopper or wall in accordance with another embodiment of the present invention.

Referring now to FIG. 10, another embodiment of an infant car seat challenge testing station is referenced generally by numeral 14. Station 14 can be configured as any of the embodiments shown in FIGS. 6-9, and further includes a stopper or wall 48 disposed between end 46 of cushion 40 and side wall 23B of open-top receptacle 23. In general, wall 48 simulates a lower portion of a car's seat backrest such that an infant car seat placed on cushion 40 has its front edge abutting wall 48 just as if the infant car seat were positioned on the back seat of a car. Wall 48 should not extend higher than the front edge of an infant car seat so a challenge test administrator can easily see an infant in the infant car seat as a challenge test proceeds.

Figure 11:
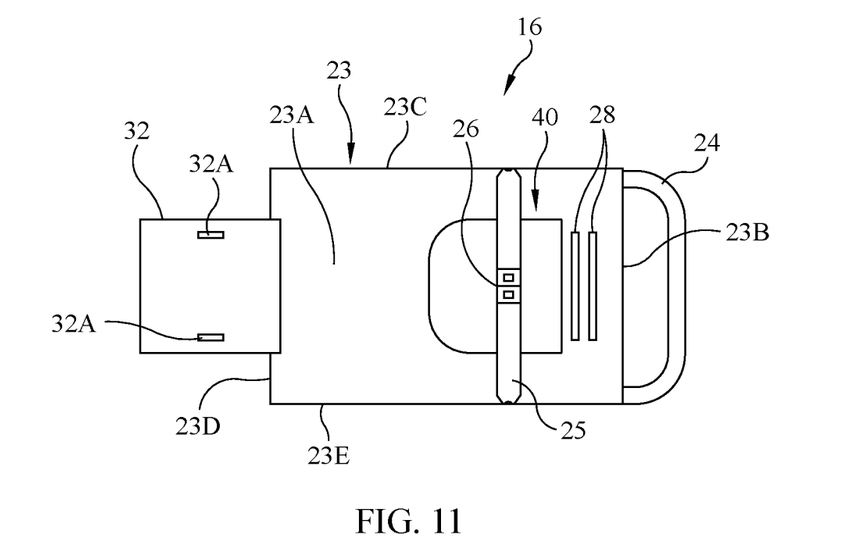
FIG. 11 is a top view of an infant car seat challenge testing station that can support multiple positions of the seat-back simulating stopper or wall in accordance with another embodiment of the present invention.
Figure 12:
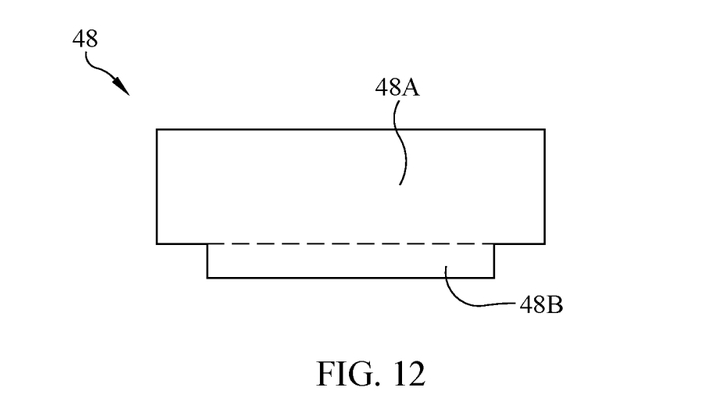
FIG. 12 is a plan view of a seat-back simulating stopper or wall for engagement in one of the slots illustrated in FIG. 11 in accordance with an embodiment of the present invention.

Wall 48 can be fixedly or removably coupled to floor 23A or cushion 40. An exemplary embodiment of a removable wall 48 will be described with simultaneous reference to FIGS. 11-12. In FIG. 11, a top view is shown of an infant car seat challenge testing station 16 having a plurality of slots 28 formed in floor 23. While two slots 28 are illustrated, it is to be understood that additional slots can be provided without departing from the scope of the present invention. Slots 28 are disposed between end 46 of cushion 40 and side wall 23B of open-top receptacle 23. For example, slots 28 can be parallel to one another and to side wall 23B. A removable wall 48 (FIG. 12) includes a longer wall portion 48A and a shorter slot engaging portion 48B. The dimensions of slot engaging portion 48B allow it to cooperate with one of slots 28 so that wall 48 can be supported and extend up from floor 23A. This allows a challenge test administrator to position wall 48 as needed depending on the configuration of an infant car seat that is to be used for a particular challenge test. It is to be understood that other types of wall supports can be used to facilitate selective positioning of wall 48 without departing from the scope of the present invention.

Although the invention has been described relative to specific embodiments thereof, there are numerous variations and modifications that will be readily apparent to those skilled in the art in light of the above teachings. For example, high-touch surfaces of the test station can be made from or covered by an antimicrobial material that passively kills bacteria deposited thereon. A proven antimicrobial material is disclosed in PCT Application No. PCT/US2013/054040. In the present invention, high-touch surfaces include side walls 23B-23E and handle 24. The present invention could be further adapted to incorporate one or more vibration mechanisms to vibrate floor 23A and/or cushion 40 using a steady-state or unsteady-state vibration profile to simulate vehicle motion. It is therefore to be understood that, within the scope of the appended claims, the invention may be practiced other than as specifically described.

What is claimed as new and desired to be secured by Letters Patent of the United States is:

1. A station for conducting an infant car seat challenge test, comprising:
   a first portion adapted to be positioned on a horizontal surface, said first portion having a top configured as an open-top receptacle;
   a resilient cushion disposed in and coupled to said open-top receptacle, said resilient cushion having a sloped top surface wherein said sloped top surface is sloped towards a first side of said open-top receptacle, said resilient cushion being adapted to support an infant car seat thereon wherein the infant car seat is positioned such that an infant seated in the infant car seat faces said first side of said open-top receptacle; and
   a second portion coupled to said first portion at a second side of said open-top receptacle, said second portion including a platform positioned above said open-top receptacle wherein said platform is adapted to support an electronic display thereon.

2. A station as in claim 1, further comprising wheels coupled to said first portion and adapted for rolling movement on the horizontal surface.

3. A station as in claim 1, further comprising a strap coupled to said first portion and adapted to secure the infant car seat in position on said sloped top surface of said resilient cushion.

4. A station as in claim 1, wherein said resilient cushion is removably coupled to said open-top receptacle.

5. A station as in claim 1, further comprising a wall disposed within and engaging said open-top receptacle, said wall positioned between said resilient cushion and said first side of said open-top receptacle, said wall adapted to engage a front of the infant car seat positioned on said resilient cushion.

6. A station as in claim 5, further comprising a plurality of wall supports coupled to said open-top receptacle between said resilient cushion and said first side of said open-top receptacle, wherein said wall is adjustably positioned between said resilient cushion and said first side of said open-top receptacle via engagement with at least one of said wall supports.

7. A station as in claim 1, wherein said second portion is adjustable relative to said first portion to adjust a position of said platform relative to said open-top receptacle.

8. A station for conducting an infant car seat challenge test, comprising:
a base adapted to be positioned on a horizontal surface;
an open-top receptacle coupled to a top of said base, said open-top receptacle having a floor and side walls coupled to a periphery of said floor;
a resilient cushion coupled to said floor of said open-top receptacle, said resilient cushion having a sloped top surface wherein said sloped top surface is sloped towards a first of said side walls, said resilient cushion being adapted to support an infant car seat thereon wherein the infant car seat is positioned such that an infant seated in the infant car seat faces said first of said side walls; and
a platform coupled to said base at a second of said side walls that is in direct opposition to said first of said side walls, said platform being positioned above said open-top receptacle, said platform being adapted to support an electronic display thereon.

9. A station as in claim 8, further comprising wheels coupled to a bottom of said base and adapted for rolling movement on the horizontal surface.

10. A station as in claim 9, further comprising a handle coupled to said first of said side walls and extending away from said open-top receptacle.

11. A station as in claim 8, further comprising a strap coupled to said floor and adapted to secure the infant car seat in position on said sloped top surface of said resilient cushion.

12. A station as in claim 8, wherein said resilient cushion is removably coupled to said floor.

13. A station as in claim 8, further comprising a stopper engaging said floor and positioned between said resilient cushion and said first of said side walls, said stopper adapted to engage a front of the infant car seat positioned on said resilient cushion.

14. A station as in claim 13, further comprising a plurality of supports at said floor between said resilient cushion and said first of said side walls, wherein said stopper is adjustably positioned via engagement with at least one of said supports.

15. A station as in claim 8, wherein said platform is adjustably coupled to said base for selective positioning of said platform relative to said open-top receptacle.

16. A station for conducting an infant car seat challenge test, comprising:
a portable base adapted to be positioned on a horizontal surface for movement there along, said base having a top configured as an open-top receptacle;
a resilient cushion disposed in and removably coupled to said open-top receptacle, said resilient cushion having a sloped top surface wherein said sloped top surface is sloped towards a first side of said open-top receptacle at an angle in a range of 6° to 17°, said resilient cushion being adapted to support an infant car seat thereon wherein the infant car seat is positioned such that an infant seated in the infant car seat faces said first side of said open-top receptacle;
a strap coupled to said open-top receptacle and adapted to secure the infant car seat in position on said sloped top surface of said resilient cushion and
a platform coupled to said open-top receptacle and positioned above said open-top receptacle wherein said platform is adapted to support an electronic display thereon.

17. A station as in claim 16, further comprising a wall disposed within and engaging said open-top receptacle, said wall positioned between said resilient cushion and said first side of said open-top receptacle, said wall adapted to engage a front of the infant car seat positioned on said resilient cushion.

18. A station as in claim 17, further comprising a plurality of wall supports coupled to said open-top receptacle between said resilient cushion and said first side of said open-top receptacle, wherein said wall is adjustably positioned between said resilient cushion and said first side of said open-top receptacle via engagement with at least one of said wall supports.

19. A station as in claim 16, wherein said platform is adjustably coupled to said base for selective positioning of said platform relative to said open-top receptacle.

20. A station as in claim 16, further comprising a handle coupled to said first side of said open-top receptacle and extending away therefrom.

* * * * *